(12) United States Patent
Abate et al.

(10) Patent No.: US 8,298,182 B2
(45) Date of Patent: Oct. 30, 2012

(54) DEVICE FOR WASHING NASAL CAVITIES WITH AN INCORPORATED PUMP

(75) Inventors: Riccardo Abate, S. Martino Della Battaglia (IT); Luigi Abate, S. Martino Della Battaglia (IT)

(73) Assignee: Flaem Nuova S.p.A., Brescia (IT)

( * ) Notice: Subject to any disclaimer, the term of this patent is extended or adjusted under 35 U.S.C. 154(b) by 0 days.

(21) Appl. No.: 12/937,742

(22) PCT Filed: Apr. 3, 2009

(86) PCT No.: PCT/IT2009/000143
§ 371 (c)(1),
(2), (4) Date: Oct. 14, 2010

(87) PCT Pub. No.: WO2009/128109
PCT Pub. Date: Oct. 22, 2009

(65) Prior Publication Data
US 2011/0040250 A1    Feb. 17, 2011

(30) Foreign Application Priority Data

Apr. 15, 2008   (IT) .............................. BS2008A0081

(51) Int. Cl.
*A61M 37/00* (2006.01)
(52) U.S. Cl. ...................................................... 604/140
(58) Field of Classification Search ............ 128/200.11–200.23; 604/27, 28, 36, 140
See application file for complete search history.

(56) References Cited

U.S. PATENT DOCUMENTS

| 5,394,866 | A | * | 3/1995 | Ritson et al. | 128/200.14 |
| 5,743,252 | A | * | 4/1998 | Rubsamen et al. | 128/200.14 |
| 6,520,931 | B2 | * | 2/2003 | Suh | 604/73 |
| 6,698,421 | B2 | * | 3/2004 | Attolini | 128/200.14 |
| 6,732,731 | B1 | * | 5/2004 | Tseng | 128/200.21 |
| 7,862,536 | B2 | * | 1/2011 | Chen et al. | 604/73 |
| 2001/0002592 | A1 | * | 6/2001 | Attolini | 128/200.21 |
| 2002/0022797 | A1 | * | 2/2002 | Suh | 604/48 |
| 2002/0043958 | A1 | * | 4/2002 | Yamaguchi et al. | 320/113 |
| 2011/0041269 | A1 | * | 2/2011 | Iwahori | 15/22.1 |
| 2011/0068738 | A1 | * | 3/2011 | Gomi et al. | 320/108 |

* cited by examiner

Primary Examiner — Christopher D Koharski
Assistant Examiner — Aarti B Berdichevsky
(74) Attorney, Agent, or Firm — McGlew and Tuttle, P.C.

(57) ABSTRACT

The invention concerns a device for washing nasal cavities by a nebulized liquid, that comprises a main body (12), a tank for liquids (14) including at least a nebulization chamber (23), and means of collection and nebulization of the treatment liquid from said nebulization chamber and delivery of the nebulized liquid towards the nasal cavities with the help of a flow of air under pressure generated by a compressor group. The main body (12) has a cavity and the compressor group (18), a piloting electronic circuit (20) and an electric battery system (31) are all on board of a single support housed and retained in the cavity of said main body.

20 Claims, 4 Drawing Sheets

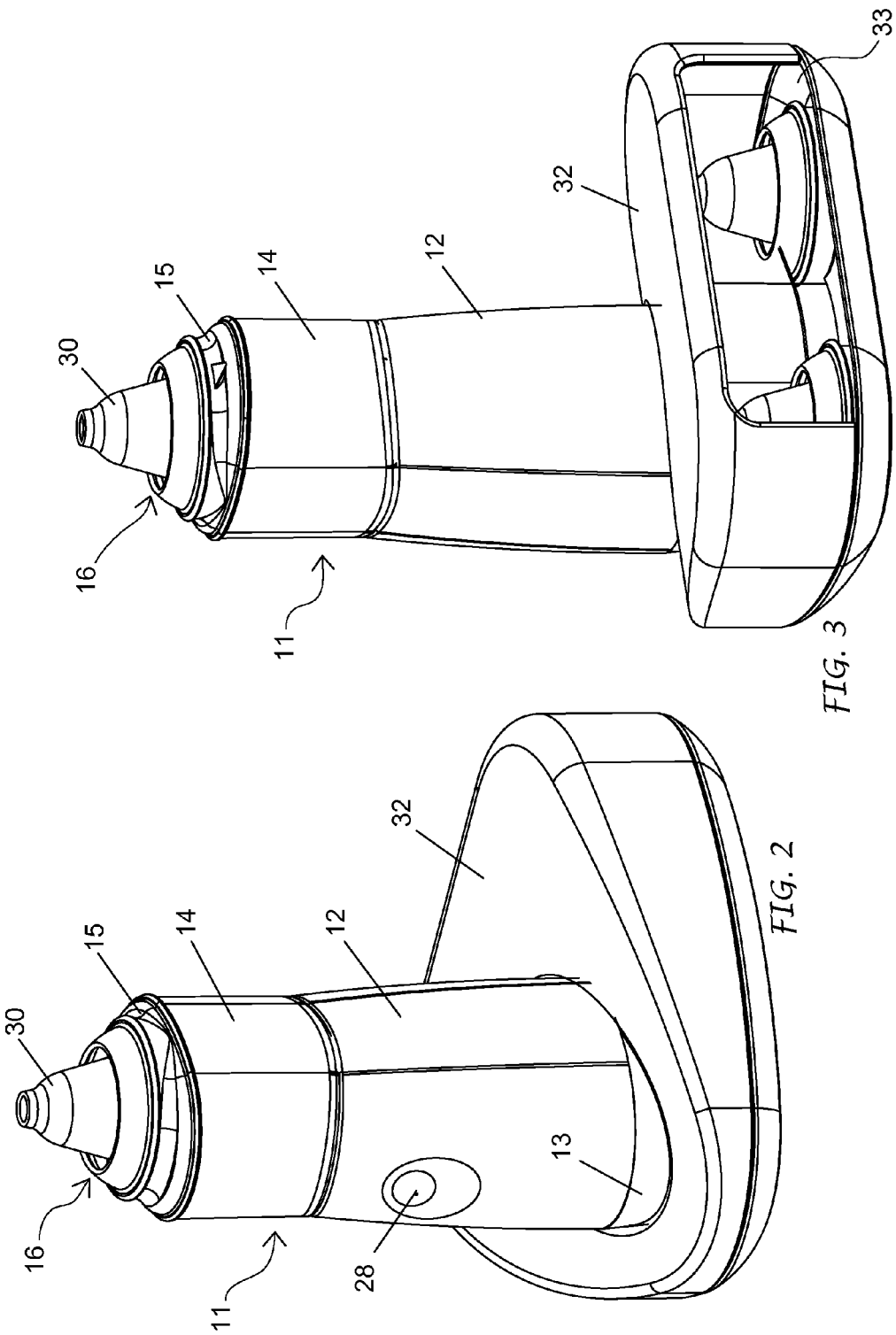

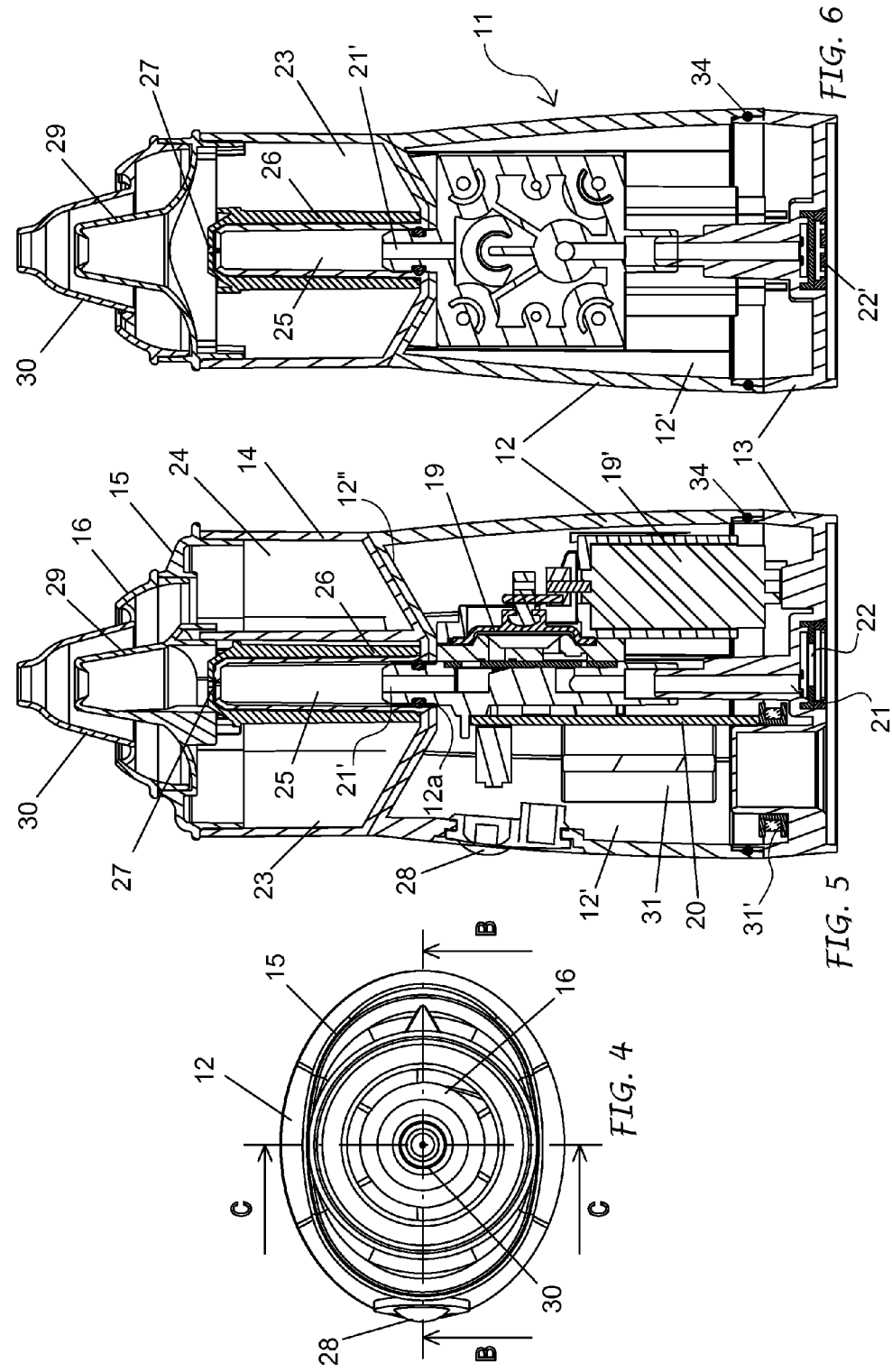

DEVICE FOR WASHING NASAL CAVITIES WITH AN INCORPORATED PUMP

CROSS REFERENCE TO RELATED APPLICATIONS

This application is a United States National Phase application of International Application PCT/IT2009/000143 and claims the benefit of priority under 35 U.S.C. §119 of Italian Patent Application BS2008A000081 filed Apr. 15, 2008, the entire contents of which are incorporated herein by reference.

FIELD OF THE INVENTION

This invention concerns in general treatment liquid nebulizing devices, and refers in particular to a device for delivery a liquid for washing nasal cavities, also known as a nasal douche.

BACKGROUND OF THE INVENTION

For the washing, that is the irrigation, of the nasal cavities, devices basically comprising a body defining a nebulizing chamber, a sprayer nozzle, an injector, and a chamber to receive the catarrhal matter are already well known.

In a previous patent IT 252109 by the same Applicant, a so-called nasal douche was proposed which was able, through an original configuration, arrangement and combination of its components, to assist the loading of the washing liquid in the respective chamber, to facilitate the possibility of dismounting the parts so as to be able to access and clean them without difficulty and make assembly easy to perform.

This device, however, like the others of the same type, to receive the necessary flow of air in order to function, must be connected at least pneumatically to an external system, be it a centralized circuit or equipment comprising a compressor with an electric circuit. Such equipment, furthermore, besides being cumbersome and bulky to carry, must be connected to the electric system with consequent ties regarding the usage position. In other words a nasal douche according to the traditional embodiments cannot be used autonomously, but always in association and connected to external equipment.

Other devices for washing the nasal cavities representative of the actual state of the technique have been disclosed, for example, in the documents EP1 180 373, U.S. 2003/089367 and EP 1 106 195, where, however, the functional components of every devices are lodged in a body, but they are not integrated on a single support and they have not hermetic sealing.

SUMMARY OF THE INVENTION

One object of this invention is to implement a device for washing the nasal cavities to make it really portable, straightforward and easy to use, and usable autonomously in any place without ties or external connections of any type and to make it easier to use and to clean/disinfect, being this aspect very important in the medical field to avoid potential infections induced from the devices to the patient.

Another object is to provide a device configured so that it is able to contain all the functional components required for its use, advantageously with hermetic sealing where is in fact provided a protection of the various components during the device washing and disinfecting operations by liquid substances.

A further object is to provide a nasal washing device including also the rechargeable feed batteries and also provided with a battery charger, the latter with the dual function of supporting the nasal irrigation device at least while it is being recharged and to contain the accessories for the device.

Said objects and the implicit advantages deriving from them are reached with a nebulizing device for washing the nasal cavities having a main body, a tank of liquids (14) above the main body and possibly including at least a nebulization chamber containing the washing liquid, and a means for drawing and nebulizing the treatment liquid from the nebulization chamber and supplying the nebulized liquid towards the nasal cavities with the help of a flow of air under pressure generated by a compressor group which is controlled by a piloting electronic circuit powered by an electric battery system connectable to a recharger unit. The main body has a cavity closed by a sealing base cap and the compressor group, piloting electronic circuit and electric battery system are all on board of a single support housed and retained in the cavity of said main body.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a perspective view from one angle of the device in FIG. 1 when assembled and inserted on a support base;

FIG. 3 is perspective view from another angle of the device in FIG. 1 when assembled and inserted on a support base;

FIG. 4 is a top view of the device;

FIG. 5 is a sectional view according to arrows B-B in FIG. 4;

FIG. 6 is a sectional view according to arrows C-C in FIG. 4;

DESCRIPTION OF THE PREFERRED EMBODIMENTS

Figure 1:
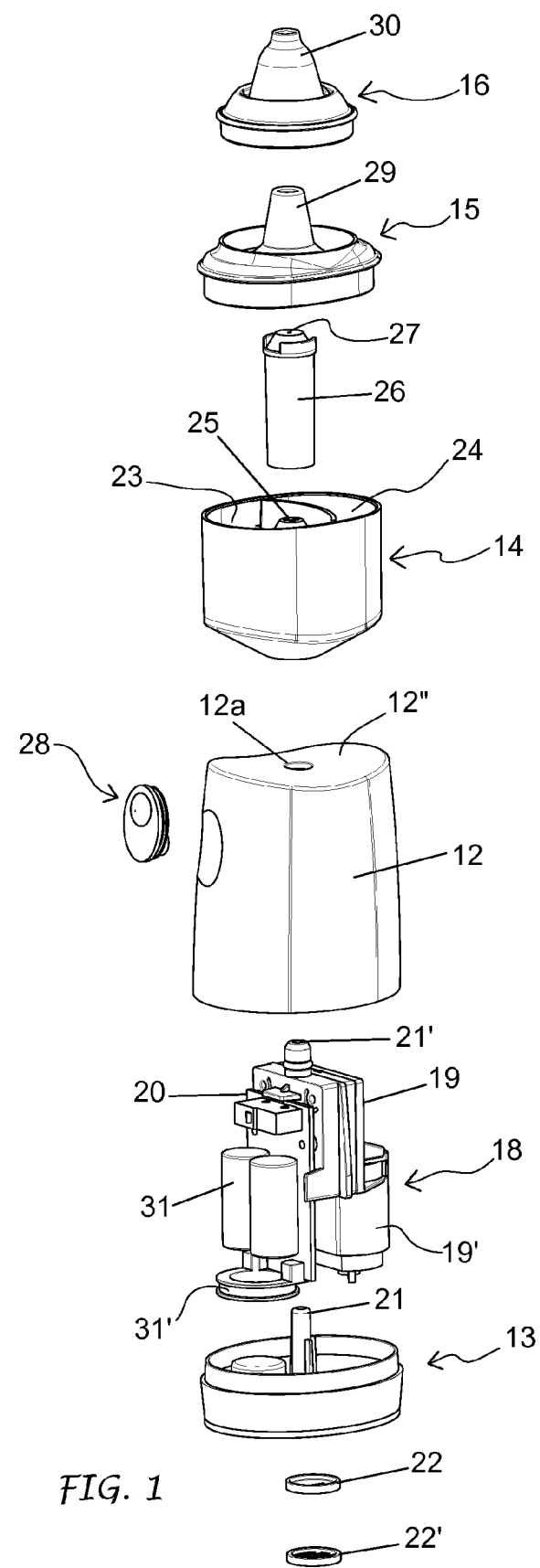
FIG. 1 is an exploded view in perspective, of the components of the nasal washing device according to a first embodiment.
Figures 7, 8:
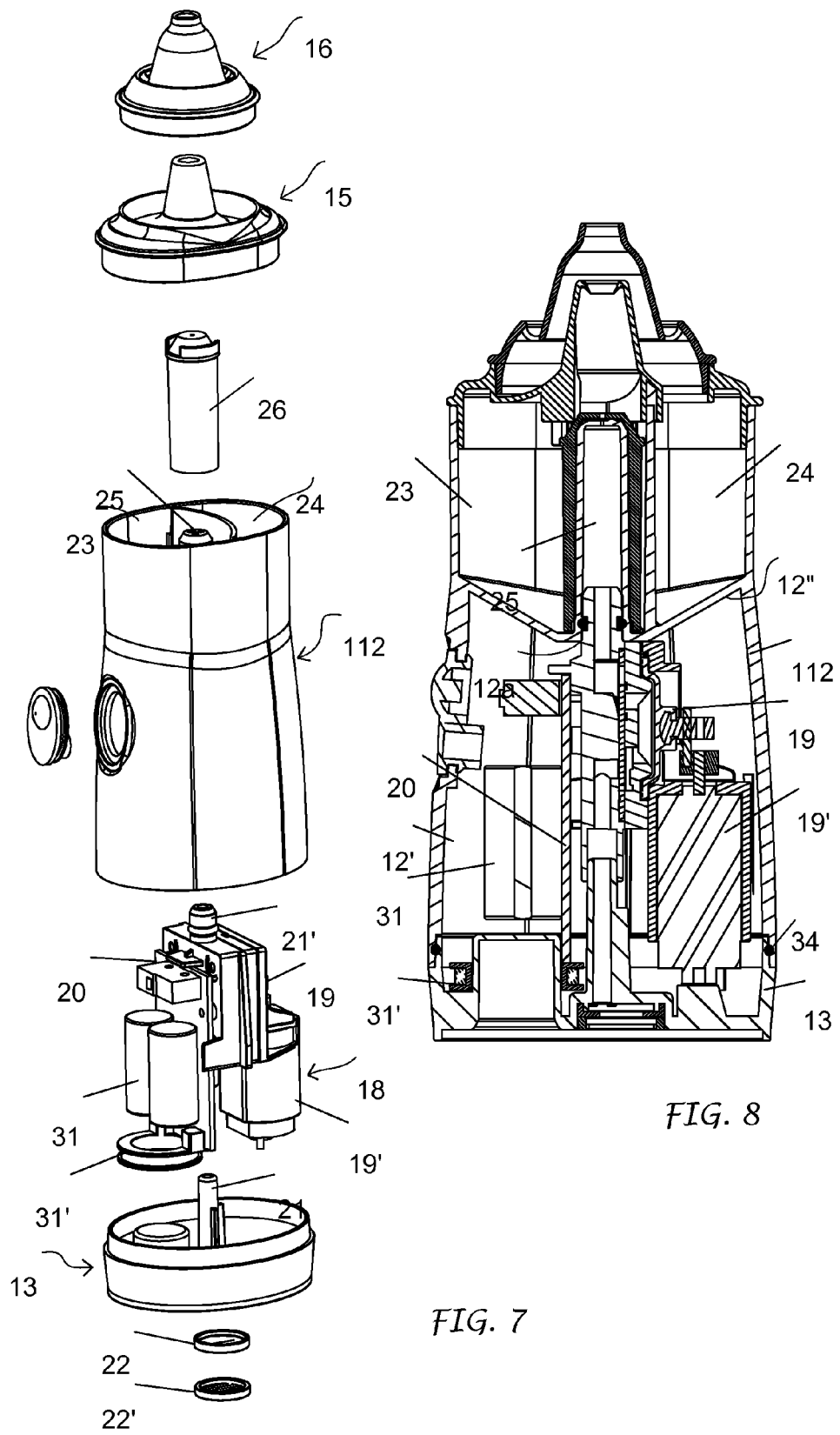
FIG. 7 is an exploded view of the nasal washing device according to a construction variation.
FIG. 8 is a sectional view of the device in FIG. 7 when assembled.

In the versions represented in FIGS. 1-6, the nasal washing device 11 comprises a main body 12, a base cap 13, a tank 14 for the treatment liquid, a cover or separator 15 above said tank and an adapter 16 above the separator. All these components can for example be made of plastic material and configured to mate by superimposition.

In this example, the main body 12 and the tank 14 are components made separately and superimposed and they are opportunely connected to each other. In particular, the body 12 is hollow and delimits a cavity 12', which is closed, at the bottom, by the base cap 13 and, at the top, by a wall 12" sloping conically downwards where it delimits a central opening 12a.

In the cavity 12' of the main body 12 is housed a compressor group 18 that includes a pump 19, powered by a respective electric motor 19' and designed to generate a flow of compressed air, and an electric circuit board 20 piloting the device. The pump 19 communicates, at the bottom, with an air intake passage 21 facing towards a possible intake valve 22 mounted on the base cap 13 and, at the top, with an air delivery nozzle 21' that extends upwards through the central 12a of the top conical wall 12" of the main body. To the base cap 13, in line, where provided, with the intake valve 22, a perforated cover 22' can be applied protecting said valve, which also has the purpose of protecting the inside of the device against the penetration of liquids from the outside, in particular when the device is washed.

The tank 14 is divided into two chambers, which are side by side: one nebulizer chamber 23 containing the liquid to be nebulized, and a collection chamber 24 for possible catarrhal substances and washing matters returning from the nasal cavities. From the bottom of the nebulizer chamber 23, a conduit 25 extends upwards, which engages under pressure and by sealing with the air delivery nozzle 21' of the pump. Around the conduit 25 a tubular cap 26 is mounted, which is open radially towards the nebulizer chamber 23, near its bottom, to draw up the liquid it contains, while at the top it flows into a nebulizer nozzle or pisper 27 which is above and in line with the delivery nozzle of the air 21' from the pump.

Advantageously, the pump group 18 is connected to and electrical supplied by the batteries 31 also housed in the cavity of the main body 12, so as to allow, as predicted, use of the device without the need for electric cables and/or restraints of any type. The batteries 31, even if the disposable type could be used, preferably is given to the rechargeable type controlled by the piloting board 20 by means of an induction electromagnetic recharge unit 31' type that mates with a hollow portion of the base cap 13 and which is provided to connect up to an inductor—not shown—placed in a supporting element 32 acting as a rest for the device in an erect position, both during recharging and when it is not used.

For its use, the device is activated by a control switch 28 placed on one side of the main body that controls the feed of current to the electronic piloting circuit and so as to be able deactivate/activate the pump. When it is activated, the pump generates a flow of air which, by re-ascending the conduit 25, suck, due to suction pressure, the washing liquid from the bottom of the chamber 23, forcing it through the nebulizer nozzle, or pisper, 27. A nebulized liquid is formed in this way and is suitable for washing the nasal cavities, which exits from the device through a concentrator 29 and a delivery member 30 defined respectively by the separator 15 and by the summit adapter 16.

It should be underlined that between the base cap 13 and the main body 12 a seal 34 can be provided so as to be able to wash the device where necessary, without problems for the internal components and the electronic circuit. Furthermore, the supporting element can also be a space 33 in which to place accessories or anything else needed by the device.

In the variation shown in FIGS. 7 and 8, the disposition and combination of the other components still holding, besides designed with the same reference numbers used in the previous figures, in the nasal washing device the main body 112 and the tank for liquids instead of being made up of separate elements and then joined together are advantageously a whole integral element.

While specific embodiments of the invention have been described in detail to illustrate the application of the principles of the invention, it will be understood that the invention may be embodied otherwise without departing from such principles.

The invention claimed is:

1. A device for washing nasal cavities by a nebulized treatment liquid, the device comprising:

a main body;

a tank of liquids above the main body and said tank including at least one nebulization chamber containing a washing liquid;

a means for drawing and nebulizing the treatment liquid from said nebulization chamber and supplying the nebulized liquid towards the nasal cavities with a flow of air under pressure generated by a compressor group, said compressor group being controlled by a piloting electronic circuit powered by an electric battery system connectable to a recharger unit, said main body having a cavity closed by a sealing base cap and said compressor group, said piloting electronic circuit and said electric battery system are on board a single support housed and retained in the cavity of said main body, wherein one portion of said compressor group is in communication with an outside environment via an intake passage and another portion of said compressor group is in communication with said means for drawing and nebulizing the treatment liquid via a delivery nozzle formed in said support, said intake passage being associated with an intake valve.

2. A device according to claim 1, wherein said compressor group comprises a pump with an electric control motor and said piloting electronic circuit is connected to said electric battery system through a switch.

3. A device according to claim 1, wherein said electric battery system comprises batteries, said batteries being rechargeable and said batteries being connected to a recharger unit connected in turn to an electric feeder by means of a connection system which is located and contained in an element supporting the device.

4. A device according to claim 1, wherein the intake valve of the pump is placed in said base cap in association with a protection cover.

5. A device according to claim 1, wherein the main body and the tank for liquids are made up of independent elements, superimposed and joined to each other.

6. A device according to claim 1, wherein the main body is integrally connected to the tank for liquids to form a one-piece main body tank structure.

7. A device according to claim 1, wherein said compressor group, said piloting electronic circuit and said electric battery system are directly mounted to said support.

8. A device according to claim 1, wherein the main body and the tank for liquids are made up of independent elements, superimposed and joined to each other.

9. A device according to claim 1, wherein said intake passage, at least a portion of said compressor group and said delivery nozzle form at least a portion of an air flow path.

10. A device according to claim 3, wherein the element supporting the device has at least one space for additional nasal cavity washing device parts or accessories, said additional nasal cavity washing device parts or accessories comprising one or more delivery members.

11. A device according to claim 3, wherein the recharger unit is an electromagnetic induction type recharger unit.

12. A device according to claim 11, wherein the element supporting the device has at least one space for additional nasal cavity washing device elements or accessories, said additional nasal cavity washing device parts or accessories comprising one or more delivery members.

13. A device for washing nasal cavities by a nebulized treatment liquid, the device comprising:
- a main body comprising a main body cavity and an upper main body surface, said upper main body surface defining at least a portion of said main body cavity;
- a base cap connected to said main body, said base cap closing one end of said main body cavity;
- a sealing element arranged between a portion of said base cap and a portion of said main body;
- a tank structure comprising at least one nebulization chamber, said at least one nebulization chamber comprising a washing liquid, said tank structure comprising a lower tank structure surface, said lower tank structure surface engaging said upper main body surface;
- a compressor group generating a flow of air under pressure;
- a single support arranged in said main body cavity, said single support comprising a delivery nozzle;
- an intake valve connected to said base cap;
- an intake element defining an intake passage, said intake passage being in communication with said intake valve, said intake element being connected to said base cap, said compressor group being in communication with an outside environment via said intake passage and said compressor group being in communication with means for drawing and nebulizing the treatment liquid via said delivery nozzle;
- an electric battery system, said electric battery system being connectable to a recharger unit;
- a piloting electronic circuit powered by said electric battery system, said compressor group being controlled via said piloting electronic circuit, said compressor group, said piloting electronic circuit and said electric battery system being directly mounted to said single support;
- a means for drawing and nebulizing the treatment liquid from said nebulization chamber and supplying the nebulized liquid towards the nasal cavities with said flow of air under pressure generated by said compressor group, said main body having a cavity closed by a sealing base cap.

14. A device according to claim 13, wherein said upper main body surface comprises an opening, at least a portion of said delivery nozzle being arranged in said opening.

15. A device according to claim 14, wherein said intake valve, said intake passage, at least a portion of said compressor group and said delivery nozzle define at least a portion of an air flow path.

16. A device according to claim 15, wherein a conduit is connected to said tank structure, at least a portion of said conduit being arranged in said nebulizer chamber, said conduit defining at least one portion of said air flow path, wherein a tubular element surrounds said conduit, said tubular element receiving said washing liquid from said nebulizer chamber, wherein air delivered via said air flow path mixes with said washing liquid from said tubular element to form an air washing liquid fluid mixture.

17. A device for washing nasal cavities by a nebulized treatment liquid, the device comprising:
- a main body comprising a main body cavity;
- a base cap connected to said main body, said base cap closing one end of said cavity;
- a sealing element sealing an area between said base cap and said main body, wherein said one end of said main body cavity is sealed via said sealing element;
- a tank structure comprising at least one nebulization chamber, said tank structure being arranged at a position above said main body;
- a washing liquid provided in said at least one nebulization chamber;
- a compressor group for generating a flow of air under pressure;
- a single support arranged in said main body cavity, said single support comprising a delivery nozzle;
- an intake valve connected to said base cap;
- an intake element defining an intake passage, said intake passage, said intake valve, at least a portion of said compressor group and said delivery nozzle defining at least a portion of an air flow path, said intake element being connected to said base cap, said intake valve being in direct communication with an outside environment;
- an electric battery system, said electric battery system being connectable to a recharger unit;
- a piloting electronic circuit powered by said electric battery system, said compressor group being controlled via said piloting electronic circuit, said compressor group, said piloting electronic circuit and said electric battery system being mounted to said single support;
- a means for drawing and nebulizing the treatment liquid from said nebulization chamber and supplying the nebulized liquid towards the nasal cavities with said flow of air under pressure generated by said compressor group, said main body having a cavity closed by a sealing base cap.

18. A device according to claim 17, wherein a tubular element is connected to said tank structure, at least a portion of said tubular element being arranged in said nebulizer chamber, said tubular element receiving said washing liquid from said nebulizer chamber, wherein air delivered from said air flow path mixes with said washing liquid from said tubular element to form an air washing liquid fluid mixture.

19. A device according to claim 17, wherein said intake passage, at least a portion of said compressor group, said delivery nozzle and said conduit are aligned with one another.

20. A device in accordance with claim 17, wherein said main body comprises an upper main body surface, said upper main body surface defining an opening, at least a portion of said delivery nozzle extending through said opening, said tank structure comprising a bottom surface, said bottom surface engaging said upper main body surface.

* * * * *